United States Patent
Naquet et al.

(10) Patent No.: US 11,579,147 B2
(45) Date of Patent: Feb. 14, 2023

(54) USE OF VNN1 AS A BIOMARKER AND A THERAPEUTIC TARGET IN SARCOMAS

(71) Applicants: INSERM (Institut National de la Santé et de la Recherche Médicale), Paris (FR); Université d'Aix Marseille, Marseilles (FR); Centre National de la Recherche Scientifique (CNRS), Paris (FR); Université Claude Bernard—Lyon 1, Villeurbanne (FR); Centre Leon Berard, Lyons (FR)

(72) Inventors: Philippe Naquet, Marseilles (FR); Franck Galland, Marseilles (FR); Virginie Millet, Marseilles (FR); Jean-Yves Blay, Lyons (FR); Caroline Giessner, Marseilles (FR)

(73) Assignees: INSERM (Institut National de la Santé et de la Recherche Médicale), Paris (FR); Université d'Aix Marseille, Marseilles (FR); Centre National de la Recherche Scientifique (CNRS), Paris (FR); Université Claude Bernard, Lyons (FR); Centre Leon Bernard, Lyons (FR)

( * ) Notice: Subject to any disclaimer, the term of this patent is extended or adjusted under 35 U.S.C. 154(b) by 68 days.

(21) Appl. No.: 16/649,860

(22) PCT Filed: Sep. 25, 2018

(86) PCT No.: PCT/EP2018/076019
§ 371 (c)(1),
(2) Date: Mar. 23, 2020

(87) PCT Pub. No.: WO2019/057995
PCT Pub. Date: Mar. 28, 2019

(65) Prior Publication Data
US 2021/0364518 A1    Nov. 25, 2021

(30) Foreign Application Priority Data

Sep. 25, 2017  (EP) .................................. 17306259

(51) Int. Cl.
| | |
|---|---|
| *A61K 31/19* | (2006.01) |
| *A61K 31/16* | (2006.01) |
| *A61K 31/131* | (2006.01) |
| *G01N 33/574* | (2006.01) |
| *A61P 35/00* | (2006.01) |
| *A61K 31/145* | (2006.01) |
| *A61K 31/195* | (2006.01) |
| *A61K 38/50* | (2006.01) |

(52) U.S. Cl.
CPC ..... *G01N 33/57407* (2013.01); *A61K 31/145* (2013.01); *A61K 31/195* (2013.01); *A61K 38/50* (2013.01); *A61P 35/00* (2018.01); *C12Y 305/01092* (2013.01); *G01N 33/57488* (2013.01)

(58) Field of Classification Search
CPC .... A61K 39/0011; A61K 31/19; A61K 31/16; A61K 31/131
USPC ................................ 514/19.3, 561, 626, 665
See application file for complete search history.

(56) References Cited

FOREIGN PATENT DOCUMENTS

WO    2013/120086 A1    8/2013

OTHER PUBLICATIONS

Willegger et al.; Serum creatinine and albumin predict sarcoma-specific survival in patients with myofibroblastic and fibroblastic sarcomas; Journal of Orthopaedic Research, May 9, 2017, entire article.

Hosohata et al.; "Urinary Vanin-1 as a Novel Biomarker for Early Detection of Drug-Induced Acute Kidney Injury"; Journal of Pharmacology and Experimental Therapeutics, vol. 341, No. 3, Jun. 1, 2012, pp. 656-662.

*Primary Examiner* — Raymond J Henley, III
(74) *Attorney, Agent, or Firm* — WCF IP

(57) ABSTRACT

Sarcomas are rare malignant tumors arising from the mesenchymal tissues at all body sites. The inventors show that in a mouse model of p16/p19 deficiency prone to tumor development, the absence of the mouse pantetheinase Vnn1 enhances the frequency of aggressive fibrosarcomas. They also show that reintroduction of a catalytically active form of the Vnn1 pantetheinase limits tumor growth in vivo. Interestingly, VNN1 expression in human sarcomas is associated with reduced aggressiveness and lower risk of metastatic relapse in patients. In conclusion, Vnn1 represents a novel marker of sarcoma and may modulate tumor aggressiveness by sustaining myofibroblast cell differentiation, thereby limiting evolution towards undifferentiated tumors. The present invention relates to the use of Vnn1 as a biomarker and a therapeutic target in sarcomas.

8 Claims, 5 Drawing Sheets

Figure 1:
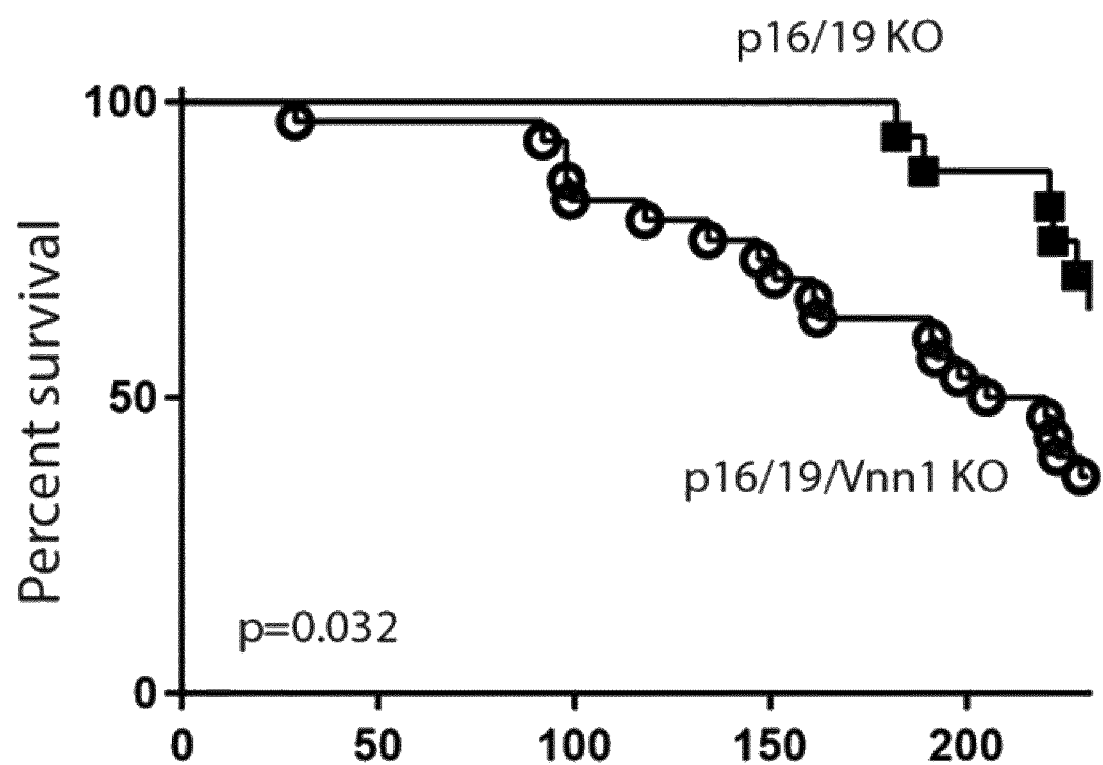

Specification includes a Sequence Listing.

SEQUENCE LISTING

<160> NUMBER OF SEQ ID NOS: 2

<210> SEQ ID NO 1
<211> LENGTH: 513
<212> TYPE: PRT
<213> ORGANISM: Homo sapiens

<400> SEQUENCE: 1

```
Met Thr Thr Gln Leu Pro Ala Tyr Val Ala Ile Leu Leu Phe Tyr Val
1               5                   10                  15

Ser Arg Ala Ser Cys Gln Asp Thr Phe Thr Ala Ala Val Tyr Glu His
            20                  25                  30

Ala Ala Ile Leu Pro Asn Ala Thr Leu Thr Pro Val Ser Arg Glu Glu
        35                  40                  45

Ala Leu Ala Leu Met Asn Arg Asn Leu Asp Ile Leu Glu Gly Ala Ile
    50                  55                  60

Thr Ser Ala Ala Asp Gln Gly Ala His Ile Ile Val Thr Pro Glu Asp
65                  70                  75                  80

Ala Ile Tyr Gly Trp Asn Phe Asn Arg Asp Ser Leu Tyr Pro Tyr Leu
                85                  90                  95

Glu Asp Ile Pro Asp Pro Glu Val Asn Trp Ile Pro Cys Asn Asn Arg
            100                 105                 110

Asn Arg Phe Gly Gln Thr Pro Val Gln Glu Arg Leu Ser Cys Leu Ala
        115                 120                 125

Lys Asn Asn Ser Ile Tyr Val Val Ala Asn Ile Gly Asp Lys Lys Pro
    130                 135                 140

Cys Asp Thr Ser Asp Pro Gln Cys Pro Pro Asp Gly Arg Tyr Gln Tyr
145                 150                 155                 160

Asn Thr Asp Val Val Phe Asp Ser Gln Gly Lys Leu Val Ala Arg Tyr
                165                 170                 175

His Lys Gln Asn Leu Phe Met Gly Glu Asn Gln Phe Asn Val Pro Lys
            180                 185                 190

Glu Pro Glu Ile Val Thr Phe Asn Thr Thr Phe Gly Ser Phe Gly Ile
        195                 200                 205

Phe Thr Cys Phe Asp Ile Leu Phe His Asp Pro Ala Val Thr Leu Val
    210                 215                 220

Lys Asp Phe His Val Asp Thr Ile Val Phe Pro Thr Ala Trp Met Asn
225                 230                 235                 240

Val Leu Pro His Leu Ser Ala Val Glu Phe His Ser Ala Trp Ala Met
                245                 250                 255

Gly Met Arg Val Asn Phe Leu Ala Ser Asn Ile His Tyr Pro Ser Lys
            260                 265                 270

Lys Met Thr Gly Ser Gly Ile Tyr Ala Pro Asn Ser Ser Arg Ala Phe
        275                 280                 285

His Tyr Asp Met Lys Thr Glu Glu Gly Lys Leu Leu Leu Ser Gln Leu
    290                 295                 300

Asp Ser His Pro Ser His Ser Ala Val Val Asn Trp Thr Ser Tyr Ala
305                 310                 315                 320

Ser Ser Ile Glu Ala Leu Ser Ser Gly Asn Lys Glu Phe Lys Gly Thr
                325                 330                 335

Val Phe Phe Asp Glu Phe Thr Phe Val Lys Leu Thr Gly Val Ala Gly
            340                 345                 350

Asn Tyr Thr Val Cys Gln Lys Asp Leu Cys Cys His Leu Ser Tyr Lys
        355                 360                 365
```

Met Ser Glu Asn Ile Pro Asn Glu Val Tyr Ala Leu Gly Ala Phe Asp
370                 375                 380

Gly Leu His Thr Val Glu Gly Arg Tyr Tyr Leu Gln Ile Cys Thr Leu
385                 390                 395                 400

Leu Lys Cys Lys Thr Thr Asn Leu Asn Thr Cys Gly Asp Ser Ala Glu
                405                 410                 415

Thr Ala Ser Thr Arg Phe Glu Met Phe Ser Leu Ser Gly Thr Phe Gly
                420                 425                 430

Thr Gln Tyr Val Phe Pro Glu Val Leu Ser Glu Asn Gln Leu Ala
                435                 440                 445

Pro Gly Glu Phe Gln Val Ser Thr Asp Gly Arg Leu Phe Ser Leu Lys
450                 455                 460

Pro Thr Ser Gly Pro Val Leu Thr Val Thr Leu Phe Gly Arg Leu Tyr
465                 470                 475                 480

Glu Lys Asp Trp Ala Ser Asn Ala Ser Ser Gly Leu Thr Ala Gln Ala
                485                 490                 495

Arg Ile Ile Met Leu Ile Val Ile Ala Pro Ile Val Cys Ser Leu Ser
                500                 505                 510

Trp

<210> SEQ ID NO 2
<211> LENGTH: 3844
<212> TYPE: DNA
<213> ORGANISM: Homo sapiens

<400> SEQUENCE: 2

```
agcactcatt ggacttcagc atgactactc agttgccagc ttacgtggca attttgcttt      60
tctatgtctc aagagccagc tgccaggaca cttttcactg cagctgttta gagcatgcag     120
cgatattgcc caatgccacc ctaacaccag tgtctcgtga ggaggctttg cattaatga      180 atcggaatct ggacattttg gaaggagcga tcacatcagc agcagatcag ggtgcgcata     240
ttattgtgac tccagaagat gctatttatg ctggaacttc aacagggac tctctctacc     300 catatttgga ggacatccca gaccctgaag taaactggat ccctgtaat aatcgtaaca     360 gatttggcca gaccccagta caagaaagac tcagctgcct ggccaagaac aactctatct     420
atgttgtggc aaatattggg acaagaagc atgcgatac cagtgatcct cagtgtcccc     480
ctgatggccg ttaccaatac aacactgatg tggtatttga ttctcaagga aaactggtgg     540
cacgctacca taagcaaaac cttttcatgg gtgaaaatca attcaatgta cccaaggagc     600
ctgagattgt gactttcaat accacctttg aagttttgg cattttcaca tgctttgata     660
tactcttcca tgatcctgct gttaccttgg tgaaagattt ccacgtggac accatagtat     720
tcccaacagc ttgatgaat gttttgccac atttgtcagc tgttgaattc cactcagctt     780
gggctatggg catgagggtc aatttccttg catccaacat acattacccc tcaaagaaaa     840
tgacaggaag tggcatctat gcacccaatt cttcaagagc atttcattat gatatgaaga     900
cagaagaggg aaaactcctc ctctcgcaac tggattccca cccatcccat tctgcagtgg     960
tgaactggac ttcctatgcc agcagtatag aagcgctctc atcaggaaac aaggaattta    1020
aaggcactgt ctttttcgat gaattcactt ttgtgaagct cacaggagtt gcaggaaatt    1080
atacagtttg tcagaaagat ctctgctgtc atttaagcta caaatgtct gagaacatac    1140 caaatgaagt gtacgctcta ggggcatttg acggactgca cactgtggaa gggcgctatt    1200
atctacagat ttgtaccctg ttgaaatgta aaacgactaa tttaaacact tgcggtgact    1260
```

```
cagctgaaac agcttctacc aggtttgaaa tgttctccct cagtggcact ttcggaaccc    1320
agtatgtctt tcctgaggtg ttgctgagtg aaaatcagct tgcacctgga gaatttcagg    1380
tgtcaactga cggacgcttg tttagtctga agccaacatc cggacctgtc ttaacagtaa    1440
ctctgtttgg gaggttgtat gagaaggact gggcatcaaa tgcttcatca ggcctcacag    1500
cacaagcaag aataataatg ctaatagtta tagcacctat tgtatgctca ttaagttggt    1560
agaatattga cttttctct tttttatttg ggataattta aaaaatgatg gatgagaaaa     1620
gaaagattgg tccgggttaa tattatcctc tagtataagt gaattactag tttctcttta    1680
tttagacaaa cacacacaca ccagataata taaacttaat aaattatctg ttaatgtaga    1740
ttttattaa aaaactatat ttgaacattg gtctttcttg gacgtgagct aattatatca     1800
aataagtatc acaaatcttt tacgcagaag aaataaaaac tacgggtaga aaacataaga    1860
actatcataa aatttactta caaggaggct gctcttgtta ccacttttat tatattacgt    1920
atcacttatt cagctctgct gaaaatttcc aatgactttg tttgtttgct cttttgttt     1980
tttacctaaa caatacattt tgattctctt gtgggttgat aatgtctccc caaaatttac    2040
atgttgaagc acctcagaat gtgactgtat ttggagacag ggtctttaaa gaggtaaaat    2100
aaggtcatta ggatagaccc taattcaata tgactgatga tcataaaaga agaggcgagt    2160
agggcacaac aggcacaaag ggagaccata aggagacaca gaggaaggac aactctttac    2220
aagctaagaa gagagggcct cagaagaaac caaccctgcc aacaccttga tcttggactt    2280
ccagcctcca aaactatgag aaataaattt ctattgttta agtcacccag tccatggtac    2340
tttgttaggc agccctggca aatgaatcaa agacccattc ctgttcctct ccccaccact    2400
actgttttct actgtaatct gaagcttcaa caaaaggctt acctggtaag aatattcagc    2460
tggtctgggt cctcaagact ccaatagaca ctcttagaga aggattgctg atggattgat    2520
agtgaaacca ttagatcatt gaattcctct ggaattagaa aaccagagag tcccatttta    2580
agaaattaga tatttaatat agcattgtgt gttctatttt agtaacagca gaatctcttg    2640
acattacaca actcagtgaa acaacatcat ttaagccaaa atatctccca actgactgat    2700
agactctgag cactaatatc atagtgctgt gatgatggac aattacatag taccgataac    2760
agccatgcac tgtgcaaagc atgcccttct gcacaggaga gcaaggcact tgcagtagtg    2820
atctatgcca gcaaaacatc attttgagac aaacattttt gtggcagatg ttttcctaa    2880
aaagtactat atcatccaag aaatatttga gtaaaatccc ttgttctttt gggtgacatt    2940
aactgacatt tgcttttttt caagacctaa tagaaaataa gaaagcccat aatgtattta    3000
gaaacaggaa tcctcagagc aattctctgt attctcatat aatttcaatg taaaacagaa    3060
aacatattga tgtgttggtg ataggcttga attattaaaa acttcaaaaa catcctaagt    3120
gtttctttt tgctcaacgt tgtcaactat agtaggtctc ccttgtggtg taatgaattg     3180
cccccaaact attatcttaa aacaacaaac atttattatc ttatagcatt tctgagggtc    3240
aggatctggg actggcttag tggagttgtt ctggatcagg gcctttggaa agttgtagtt    3300
aacttgtccc cagggctgcc atcatctcaa ggctcgggtg gggctggaga aaatctgctt    3360
ctcagctcac tcacggcggt tgccaggcct ccattcttta ggatgctaga aaaactttca    3420
taaaatgtca tctggcttct cctagagcaa tgatactgag agagaaagca catgagagaa    3480
agagcgaggg aacttggatg taagccacag tcttttgaaaa cctaatcaca gaagtgacat    3540
ctcttcttcc acatgatgtt ggtcacatgg accaacaatg gcacaacgtg gacagaatca    3600
aacagagttg agaatatcag gaggtggggc ttcatggggg ccattttgga tgctatcata    3660
```

```
gtgaatatat gtatttatat ttatatctgt atatattgca atgtaattta aaaaatagga    3720
ttgttttcct tttctttttg ctatatgtga tatgtatttc aaaatacact cccaatagtt    3780
acgtctgaaa agcactacac taaaaaactt tctatacatt gaataattaa attaaataat    3840
ctaa                                                                 3844
```

USE OF VNN1 AS A BIOMARKER AND A THERAPEUTIC TARGET IN SARCOMAS

FIELD OF THE INVENTION

The present invention relates to the use of Vnn1 as a biomarker and a therapeutic target in sarcomas.

BACKGROUND OF THE INVENTION

Sarcomas are rare malignant tumors arising from the mesenchymal tissues at all body sites. Soft tissue sarcomas (STS) represent a very heterogeneous family of tumors which derive from mesenchymal cells. These tumors appear to arise from malignant precursor cells which can then differentiate along one or several lineages, such as muscle, adipose, fibrous, cartilage, or vascular tissue. Their classification, insights into molecular pathogenesis, and definition of optimal treatment strategies have evolved considerably over the past 10 to 25 years. There are more than 80 histologic subtypes of STS, many of which are associated with distinctive clinical profiles that may have important implications for therapy and prognosis. The small number of cases seen and the great diversity in anatomic site, histopathology, and biology complicate understanding of the natural history of these tumors and their response to diverse therapies. There is thus a need to identify biomarkers that will allow stratifying the patients, especially in regards to their survival time. Numerous genetic alterations involving p53, Rb, Ink4a/ARF are associated with STS leading to the definition of genomic profiles linked to prognosis. Mutations in the Ras pathway have been identified in aggressive rhabdomyosarcomas {Zhang, 2013}. These mutations are associated with dramatic changes in redox regulation linked to increased mitochondrial activity which might contribute to tumor prognostic. Vnn1 pantetheinase was identified as a key regulator of metabolic adaptation of tissues to stress in diseases {Naquet, 2014}. This inducible enzyme hydrolyzes pantetheine, a degradative product of Coenzyme A (CoA), to regenerate the CoA precursor pantothenate (ie vitamin B5) and cysteamine, a small aminothiol which post-translationally modifies target proteins and impacts signaling. Whereas this pathway is playing a limited role under homeostatic conditions, its induction reflects a local adaptation to metabolic or oxidative stress as shown in gut {Berruyer, 2006; Martin, 2004}, liver {van Diepen, 2014} {Ferreira, 2016} and connective tissue {Dammanahalli, 2012} where it participates to healing processes. However, the involvement of Vnn1 in the progression of sarcoma has not yet been investigated.

SUMMARY OF THE INVENTION

The present invention relates to the use of Vnn1 a biomarker and a therapeutic target in sarcomas. In particular, the present invention is defined by the claims.

DETAILED DESCRIPTION OF THE INVENTION

The inventors show that in a mouse model of p16/p19 deficiency prone to tumor development, the absence of the mouse pantetheinase Vnn1 enhances the frequency of aggressive fibrosarcomas. To explore the mechanism of Vnn1-mediated impact on fibrosarcoma, they developed myofibroblast cell lines from p16/p19/Vnn1 deficient mice. Upon transfection with oncogenic RasV12 and after grafting in mice, these cell lines grow as undifferentiated fibrosarcomas. Reintroduction of a catalytically active form of the Vnn1 pantetheinase limits tumor growth in vivo. Furthermore, the developing Vnn1 positive fibrosarcomas remain differentiated. This phenotype is associated with anatomopathological features of grade 1 fibrosarcoma, expression of differentiation markers of myofibroblast activation and high levels of profibrogenic cytokines such as CCL6 and IL-16. Finally, since Vnn1 participates to coenzyme A metabolism, the inventors explored the metabolomics signature of fibrosarcomas. Tumors developing in the absence of Vnn1 overexpress genes associated with aerobic glycolysis and lactate production, markers commonly associated with tumor growth and adaptation to hypoxia. Interestingly, VNN1 expression in human sarcomas is associated with reduced aggressiveness and lower risk of metastatic relapse in patients. In conclusion, Vnn1 represents a novel marker of sarcoma and may modulate tumor aggressiveness by sustaining myofibroblast cell differentiation, thereby limiting evolution towards undifferentiated tumors.

Accordingly, the first object of the present invention relates to a method of predicting the survival time of a patient suffering from a sarcoma comprising, i) determining the activity or expression level of Vnn1 in a tumor tissue sample obtained from the patient, ii) comparing the level determined at step i) with a predetermined reference value and iii) concluding that the patient will have a long survival time when the level determined at step i) is higher than the predetermined reference value or concluding that the patient will have a short survival time when the level determined at step i) is lower than the predetermined reference value.

As used herein, the term "sarcoma" has its general meaning in the art and refers to a tumor which is made up of a substance like the embryonic connective tissue and is generally composed of closely packed cells embedded in a fibrillar or homogeneous substance. Example of sarcomas includes chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma. In some embodiments, the patient suffers from soft tissue sarcoma. In some embodiments, the patient suffers from a fibrosarcoma.

The method of the present invention is particularly suitable for predicting the duration of the overall survival (OS), progression-free survival (PFS) and/or the disease-free survival (DFS) of the patient. Those of skill in the art will recognize that OS survival time is generally based on and expressed as the percentage of people who survive a certain type of cancer for a specific amount of time. Cancer statistics often use an overall five-year survival rate. In general, OS rates do not specify whether cancer survivors are still undergoing treatment at five years or if they've become cancer-free (achieved remission). DSF gives more specific information and is the number of people with a particular cancer who achieve remission. Also, progression-free survival (PFS) rates (the number of people who still have cancer, but their disease does not progress) includes people who may have had some success with treatment, but the cancer has not disappeared completely. As used herein, the expression "short survival time" indicates that the patient will have a survival time that will be lower than the median (or mean) observed in the general population of patients suffering from said cancer. When the patient will have a short survival time, it is meant that the patient will have a "poor prognosis". Inversely, the expression "long survival time" indicates that the patient will have a survival time that will be higher than the median (or mean) observed in the general population of patients suffering from said cancer. When the patient will have a long survival time, it is meant that the patient will have a "good prognosis".

As used herein, the term "tumor tissue sample" means any tissue tumor sample derived from the patient. Said tissue sample is obtained for the purpose of the in vitro evaluation. In some embodiments, the tumor sample may result from the tumor resected from the patient. In some embodiments, the tumor sample may result from a biopsy performed in the primary tumour of the patient. In some embodiments, the tumor tissue sample encompasses (i) a global primary tumor (as a whole), (ii) a tissue sample from the center of the tumor, or (iii) a tissue sample from the tissue directly surrounding the tumor which tissue may be more specifically named the "invasive margin" of the tumor. In some embodiments, the tumor tissue sample, encompasses pieces or slices of tissue that have been removed from the tumor or following the collection of a tissue sample for biopsy, for further quantification of one or several biological markers, notably through histology or immunohistochemistry methods, and through methods of gene or protein expression analysis, including genomic and proteomic analysis. The tumor tissue sample can be subjected to a variety of well-known post-collection preparative and storage techniques (e.g., fixation, storage, freezing, etc.) prior to determining the expression level of the gene of interest. Typically the tumor tissue sample is fixed in formalin and embedded in a rigid fixative, such as paraffin (wax) or epoxy, which is placed in a mould and later hardened to produce a block which is readily cut. Thin slices of material can be then prepared using a microtome, placed on a glass slide and submitted e.g. to immunohistochemistry (IHC) (using an IHC automate such as BenchMark® XT or Autostainer Dako, for obtaining stained slides). The tumour tissue sample can be used in microarrays, called as tissue microarrays (TMAs). TMA consist of paraffin blocks in which up to 1000 separate tissue cores are assembled in array fashion to allow multiplex histological analysis. This technology allows rapid visualization of molecular targets in tissue specimens at a time, either at the DNA, RNA or protein level. TMA technology is described in WO2004000992, U.S. Pat. No. 8,068,988, Olli et al 2001 Human Molecular Genetics, Tzankov et al 2005, Elsevier; Kononen et al 1198; Nature Medicine.

As used herein, the term "Vnn1" or "vanin-1" has its general meaning in the art and refers to a pantetheinase that catalyzes the hydrolysis of pantetheine to produce pantothenic acid (vitamin B5) and cysteamine. Vnn1 is encoded by the VNN1 gene (Gene ID: 8876). The term is also known as HDLCQ8; or Tiff66. An exemplary human amino acid sequence of Vnn1 is represented by the NCBI reference sequence NP_004657.2 (SEQ ID NO:1) and an exemplary human nucleic acid sequence of Vnn1 is represented by the NCBI reference sequence NM_004666.2 (SEQ ID NO:2).

```
                                                                    SEQ ID NO: 1
    1   mttqlpayva illfyvsras cqdtftaavy ehaailpnat ltpvsreeal almnrnldil
   61   egaitsaadq gahiivtped aiygwnfnrd slypyledip dpevnwipcn nrnrfgqtpv
  121   qerlsclakn nsiyvvanig dkkpcdtsdp qcppdgryqy ntdvvfdsqg klvaryhkqn
  181   lfmgenqfnv pkepeivtfn ttfgsfgift cfdilfhdpa vtlvkdfhvd tivfptawmn
  241   vlphlsavef hsawamgmrv nflasnihyp skkmtgsgiy apnssrafhy dmkteegkll
  301   lsqldshpsh savvnwtsya ssiealssgn kefkgtvffd eftfvkltgv agnytvcqkd
  361   lcchlsykms enipnevyal gafdglhtve gryylqictl lkckttnlnt cgdsaetast
  421   rfemfslsgt fgtqyvfpev llsenqlapg efqvstdgrl fslkptsgpv ltvtlfgrly
  481   ekdwasnass gltaqariim liviapivcs lsw SEQ ID NO: 2
    1   agcactcatt ggacttcagc atgactactc agttgccagc ttacgtggca attttgcttt
   61   tctatgtctc aagagccagc tgccaggaca cttcactgc agctgtttat gagcatgcag
  121   cgatattgcc caatgccacc ctaacaccag tgtctcgtga ggaggctttg gcattaatga
  181   atcggaatct ggacattttg gaaggagcga tcacatcagc agcagatcag ggtgcgcata
  241   ttattgtgac tccagaagat gctatttatg gctggaactt caacagggac tctctctacc
  301   catatttgga ggacatccca gaccctgaag taaactggat ccctgtaat aatcgtaaca
  361   gatttggcca gaccccagta caagaaagac tcagctgcct ggccaagaac aactctatct
  421   atgttgtggc aaatattggg gacaagaagc catgcgatac cagtgatcct cagtgtcccc
  481   ctgatggccg ttaccaatac aacactgatg tggtatttga ttctcaagga aaactggtgg
  541   cacgctacca taagcaaaac ctttttcatgg gtgaaaatca attcaatgta cccaaggagc
```

-continued

```
 601   ctgagattgt gactttcaat accacctttg gaagttttgg catttttcaca tgctttgata
 661   tactcttcca tgatcctgct gttaccttgg tgaaagattt ccacgtggac accatagtat
 721   tcccaacagc ttggatgaat gttttgccac atttgtcagc tgttgaattc cactcagctt
 781   gggctatggg catgagggtc aatttccttg catccaacat acattacccc tcaaagaaaa
 841   tgacaggaag tggcatctat gcacccaatt cttcaagagc atttcattat gatatgaaga
 901   cagaagaggg aaaactcctc ctctcgcaac tggattccca cccatcccat tctgcagtgg
 961   tgaactggac ttcctatgcc agcagtatag aagcgctctc atcaggaaac aaggaattta
1021   aaggcactgt cttttttcgat gaattcactt tgtgaagct cacaggagtt gcaggaaatt
1081   atacagtttg tcagaaagat ctctgctgtc atttaagcta caaaatgtct gagaacatac
1141   caaatgaagt gtacgctcta ggggcatttg acggactgca cactgtgaa gggcgctatt
1201   atctacagat ttgtaccctg ttgaaatgta aaacgactaa tttaaacact tgcggtgact
1261   cagctgaaac agcttctacc aggtttgaaa tgttctccct cagtggcact tcggaaccc
1321   agtatgtctt tcctgaggtg ttgctgagtg aaaatcagct tgcacctgga gaatttcagg
1381   tgtcaactga cggacgcttg tttagtctga agccaacatc cggacctgtc ttaacagtaa
1441   ctctgtttgg gaggttgtat gagaaggact gggcatcaaa tgcttcatca ggcctcacag
1501   cacaagcaag aataataatg ctaatagtta tagcacctat tgtatgctca ttaagttggt
1561   agaatattga ctttttctct tttttatttg ggataattta aaaaatgatg gatgagaaaa
1621   gaaagattgg tccgggttaa tattatcctc tagtataagt gaattactag tttctctta
1681   tttagacaaa cacacacaca ccagataata taaacttaat aaattatctg ttaatgtaga
1741   ttttatttaa aaaactatat ttgaacattg gtctttcttg gacgtgagct aattatatca
1801   aataagtatc acaaatcttt tacgcagaag aaataaaaac tacgggtaga aaacataaga
1861   actatcataa aatttactta caaggaggct gctcttgtta ccactttat tatattacgt
1921   atcacttatt cagctctgct gaaaatttcc aatgactttg tttgtttgct cttttttgttt
1981   tttacctaaa caatacattt tgattctctt gtgggttgat aatgtctccc caaaatttac
2041   atgttgaagc acctcagaat gtgactgtat ttggagacag ggtctttaaa gaggtaaaat
2101   aaggtcatta ggatagaccc taattcaata tgactgatga tcataaaaga agaggcgagt
2161   agggcacaac aggcacaaag ggagaccata aggagacaca gaggaaggac aactctttac
2221   aagctaagaa gagagggcct cagaagaaac caaccctgcc aacaccttga tcttggactt
2281   ccagcctcca aaactatgag aaataaattt ctattgttta agtcacccag tccatggtac
2341   tttgttaggc agccctggca aatgaatcaa agacccattc ctgttcctct ccccaccact
2401   actgttttct actgtaatct gaagcttcaa caaaaggctt acctggtaag aatattcagc
2461   tggtctgggt cctcaagact ccaatagaca ctcttagaga aggattgctg atggattgat
2521   agtgaaacca ttagatcatt gaattcctct ggaattagaa aaccagagag tcccatttta
2581   agaaattaga tatttaatat agcattgtgt gttctatttt agtaacagca gaatctcttg
2641   acattacaca actcagtgaa acaacatcat ttaagccaaa atatctccca actgactgat
2701   agactctgag cactaatatc atagtgctgt gatgatggac aattacatag taccgataac
2761   agccatgcac tgtgcaaagc atgcccttct gcacaggaga gcaaggcact tgcagtagtg
2821   atctatgcca gcaaaacatc attttgagac aaacattttt gtggcagatg ttttttcctaa
2881   aaagtactat atcatccaag aaatatttga gtaaatccc ttgttctttt gggtgacatt
2941   aactgacatt tgcttttttt caagacctaa tagaaaataa gaaagcccat aatgtattta
```

```
-continued
3001    gaaacaggaa tcctcagagc aattctctgt attctcatat aatttcaatg taaaacagaa 3061    aacatattga tgtgttggtg ataggcttga attattaaaa acttcaaaaa catcctaagt 3121    gtttcttttt tgctcaacgt tgtcaactat agtaggtctc ccttgtggtg taatgaattg 3181    cccccaaact attatcttaa aacaacaaac atttattatc ttatagcatt tctgagggtc 3241    aggatctggg actggcttag tggagttgtt ctggatcagg gccifiggaa agttgtagtt 3301    aacttgtccc cagggctgcc atcatctcaa ggctcgggtg gggctggaga aaatctgctt 3361    ctcagctcac tcacggcggt tgccaggcct ccattcttta ggatgctaga aaaactttca 3421    taaaatgtca tctggcttct cctagagcaa tgatactgag agagaaagca catgagagaa 3481    agagcgaggg aacttggatg taagccacag tctttgaaaa cctaatcaca gaagtgacat 3541    ctcttcttcc acatgatgtt ggtcacatgg accaacaatg gcacaacgtg gacagaatca 3601    aacagagttg agaatatcag gaggtggggc ttcatggggg ccattttgga tgctatcata 3661    gtgaatatat gtatttatat ttatatctgt atatattgca atgtaattta aaaaatagga 3721    ttgttttcct tttcttttg ctatatgtga tatgtatttc aaaatacact cccaatagtt 3781    acgtctgaaa agcactacac taaaaaactt tctatacatt gaataattaa attaaataat 3841    ctaa
```

The measurement of the level of Vnn1 activity in the tumor tissue sample is typically carried out using standard protocols known in the art. For instance, Vnn1 is extracted from the tissue as previously reported for the pig enzyme [3]. Then pantetheinase hydrolyzing activity can be assayed by spectrophotometrically and using S-pantetheine-3-pyruvate as substrate. The enzymatic hydrolysis of this substrate leads to the formation of S-cysteamine-3-pyruvate, which cyclizes in a non-rate-limiting step to give 2H-1,4-thiazin-5,6-dihydro-3-carboxylic acid (aminoethylcysteine ketimine), a compound exhibiting a strong absorption at 296 nm. The assay is optimized with respect to pH, buffer, and substrate concentration. Cysteamine determination is typically performed on the tumor tissue for crude extraction. Two different procedures can be used for cysteamine detection: an enzymatic assay (G. Ricci, M. Nardini, R. Chiaraluce, S. Dupre, D. Cavallini J. Appl. Biochem., 5 (1983), pp. 320-329) and a high performance liquid chromatography (HPLC) detection (R. A. Garcia, L. L. Hirschberger, M. H. Stipanuk. Anal. Biochem., 170 (1988), pp. 432-440). For the last procedure, an electrochemical detector (ESA) was used: the potentials of oxidizing electrodes were 450 and 475 mV. The lower detection limits were 4 nmol/g and 0.5 nmol/g for the enzymatic and HPLC methods, respectively.

Measuring the expression level of Vnn1 can be performed by a variety of techniques well known in the art.

In some embodiments, the expressions level is measured with a flurorescently labelled pantothenate derivative, the pantothenate-7-amino-4-methylcoumarin (pantothenate-AMC) substrate (Ruan B H, Cole D C, Wu P, Quazi A, Page K, Wright J F, Huang N, Stock J R, Nocka K, Aulabaugh A, et al (2010). Analyt Biochem 399: 284-292.).

In some embodiments, the expression level is determined at nucleic acid level. Typically, the expression level of a gene may be determined by determining the quantity of mRNA. Methods for determining the quantity of mRNA are well known in the art. For example the nucleic acid contained in the samples (e.g., cell or tissue prepared from the subject) is first extracted according to standard methods, for example using lytic enzymes or chemical solutions or extracted by nucleic-acid-binding resins following the manufacturer's instructions. The extracted mRNA is then detected by hybridization (e. g., Northern blot analysis, in situ hybridization) and/or amplification (e.g., RT-PCR). Other methods of Amplification include ligase chain reaction (LCR), transcription-mediated amplification (TMA), strand displacement amplification (SDA) and nucleic acid sequence based amplification (NASBA).

In some embodiments, the methods of the invention comprise the steps of providing total RNAs extracted from and subjecting the RNAs to amplification and hybridization to specific probes, more particularly by means of a quantitative or semi-quantitative RT-PCR.

The nucleic acid primers or probes used in the above amplification and detection method may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6× SCC. SCC is a 0.15 M NaCl, 0.015 M Na-citrate).

Typically, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook—A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS), 4-amino-N-[3 vinylsulfonyl)phenyl]naphthalimide-3,5 disulfonate (Lucifer Yellow VS), N-(4-anilino-1-naphthyl)maleimide, antllranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diarninidino-2-phenylindole (DAPI); 5',5"dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulforlic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6dichlorotriazin-2-yl)aminofluorescein (DTAF), 2'7'dimethoxy-4'5'-dichloro-6-carboxyfluorescein (JOE), fluorescein, fluorescein isothiocyanate (FITC), and QFITC Q(RITC); 2',7'-difluorofluorescein (OREGON GREEN@); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716,979), the BODIPY series of dyes (dipyrromethenboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912). In addition to the fluorochromes described above, a fluorescent label can be a fluorescent nanoparticle, such as a semiconductor nanocrystal, e.g., a QUANTUM DOT™ (obtained, for example, from Life Technologies (QuantumDot Corp, Invitrogen Nanocrystal Technologies, Eugene, Oreg.); see also, U.S. Pat. Nos. 6,815,064; 6,682,596; and 6,649, 138). Additional labels include, for example, radioisotopes (such as $^3$H), metal chelates such as DOTA and DPTA chelates of radioactive or paramagnetic metal ions like Gd3+, and liposomes. Detectable labels that can be used with nucleic acid molecules also include enzymes, for example horseradish peroxidase, alkaline phosphatase, acid phosphatase, glucose oxidase, beta-galactosidase, beta-glucuronidase, or beta-lactamase. Alternatively, an enzyme can be used in a metallographic detection scheme. For example, silver in situ hyhridization (SISH) procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redoxactive agent reduces the metal ion, causing it to form a detectable precipitate. (See, for example, U.S. Patent Application Puhlication No. 2005/0100976, PCT Publication No. 2005/003777 and U.S. Patent Application Publication No. 2004/0265922). Metallographic detection methods also include using an oxidoreductase enzyme (such as horseradish peroxidase) along with a water soluble metal ion, an oxidizing agent and a reducing agent, again to form a detectable precipitate. (See, for example, U.S. Pat. No. 6,670,113).

Probes made using the disclosed methods can be used for nucleic acid detection, such as ISH procedures (for example, fluorescence in situ hybridization (FISH), chromogenic in situ hybridization (CISH) and silver in situ hybridization (SISH)) or comparative genomic hybridization (CGH). Numerous procedures for FISH, CISH, and SISH are known in the art. For example, procedures for performing FISH are described in U.S. Pat. Nos. 5,447,841; 5,472,842; and 5,427, 932; and for example, in Pir1kel et al., Proc. Natl. Acad. Sci. 83:2934-2938, 1986; Pinkel et al., Proc. Natl. Acad. Sci. 85:9138-9142, 1988; and Lichter et al., Proc. Natl. Acad.

Sci. 85:9664-9668, 1988. CISH is described in, e.g., Tanner et al., Am. .1. Pathol. 157:1467-1472, 2000 and U.S. Pat. No. 6,942,970. Additional detection methods are provided in U.S. Pat. No. 6,280,929.

In some embodiments, the nCounter® Analysis system is used to detect intrinsic gene expression. The basis of the nCounter® Analysis system is the unique code assigned to each nucleic acid target to be assayed (International Patent Application Publication No. WO 08/124847, U.S. Pat. No. 8,415,102 and Geiss et al. Nature Biotechnology. 2008. 26(3): 317-325; the contents of which are each incorporated herein by reference in their entireties). The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system. Specific reporter and capture probes are synthesized for each target. The reporter probe can comprise at a least a first label attachment region to which are attached one or more label monomers that emit light constituting a first signal; at least a second label attachment region, which is non-over-lapping with the first label attachment region, to which are attached one or more label monomers that emit light constituting a second signal; and a first target-specific sequence. Preferably, each sequence specific reporter probe comprises a target specific sequence capable of hybridizing to no more than one gene and optionally comprises at least three, or at least four label attachment regions, said attachment regions comprising one or more label monomers that emit light, constituting at least a third signal, or at least a fourth signal, respectively. The capture probe can comprise a second target-specific sequence; and a first affinity tag. In some embodiments, the capture probe can also comprise one or more label attachment regions. Preferably, the first target-specific sequence of the reporter probe and the second target-specific sequence of the capture probe hybridize to different regions of the same gene to be detected. Reporter and capture probes are all pooled into a single hybridization mixture, the "probe library". The relative abundance of each target is measured in a single multiplexed hybridization reaction. The method comprises contacting the tumor sample with a probe library, such that the presence of the target in the sample creates a probe pair—target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies). Purified reactions are typically deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. For each sample, typically 600 fields-of-view (FOV) are imaged (1376×1024 pixels) representing approximately 10 mm2 of the binding surface. Typical imaging density is 100-1200 counted reporters per field of view depending on the degree of multiplexing, the amount of sample input, and overall target abundance. Data is output in simple spreadsheet format listing the number of counts per target, per sample. This system can be used along with nanoreporters. Additional disclosure regarding nanoreporters can be found in International Publication No. WO 07/076129 and WO07/076132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No. 2010/0047924, incorporated herein by reference in its entirety.

Expression level of a gene may be expressed as absolute expression level or normalized expression level. Typically, expression levels are normalized by correcting the absolute expression level of a gene by comparing its expression to the expression of a gene that is not a relevant for determining the cancer stage of the subject, e.g., a housekeeping gene that is constitutively expressed. Suitable genes for normalization include housekeeping genes such as the actin gene ACTB, ribosomal 18S gene, GUSB, PGK1 and TFRC. This normalization allows the comparison of the expression level in one sample, e.g., a subject sample, to another sample, or between samples from different sources.

In some embodiments, the expression level of Vnn1 is determined at the protein level by any well-known method in the art. Typically, such methods comprise contacting the tumor tissue sample with at least one selective binding agent capable of selectively interacting with Vnn1. The selective binding agent may be polyclonal antibody or monoclonal antibody, an antibody fragment, synthetic antibodies, or other protein-specific agents such as nucleic acid or peptide aptamers.

For the detection of the antibody that makes the presence of the Vnn1 detectable by microscopy or an automated analysis system, the antibodies may be tagged directly with detectable labels such as enzymes, chromogens or fluorescent probes or indirectly detected with a secondary antibody conjugated with detectable labels. For example, one or more labels can be attached to the antibody, thereby permitting detection of the target protein (i.e Vnn1). Exemplary labels include radioactive isotopes, fluorophores, ligands, chemiluminescent agents, enzymes, and combinations thereof. In some embodiments, the label is a quantum dot. Non-limiting examples of labels that can be conjugated to primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase), haptens (e.g. biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g. horseradish peroxidase, alkaline phosphatase, beta-lactamase), radioisotopes (e.g. 3H, 14C, 32P, 35S or 125I) and particles (e.g. gold). The different types of labels can be conjugated to an affinity ligand using various chemistries, e.g. the amine reaction or the thiol reaction. However, other reactive groups than amines and thiols can be used, e.g. aldehydes, carboxylic acids and glutamine.

In some embodiments, immunohistochemistry is performed. Immunohistochemistry (IHC) is a staining method based on enzymatic reactions using a binding partner, such as an antibody (e.g., monoclonal or polyclonal antibodies) or other binding partner, to detect the expression of the marker of interest (i.e. Vnn1). Typically, IHC protocols include detection systems that make the presence of the markers visible, to either the human eye or an automated scanning system, for qualitative or quantitative analyses. In a direct IHC assay, binding is determined directly upon binding of the binding partner (e.g., first antibody) to the tissue or biomarker due to the use of a labeled reagent. In such methods, generally a slide-mounted tissue sample is stained with a labeled binding reagent (e.g., labeled antibody) using common IHC techniques. Thus, in exemplary IHC methods provided herein, the antibody is modified to contain a moiety capable of being detected (as described above). In some embodiments, the antibody is conjugated to a small molecule, e.g., biotin, that is detected via a labeled binding partner or antibody. In some embodiments, the IHC method is based on staining with the antibody that is detected by enzymatic staining with horseradish peroxidase. For example, the antibody can be biotinylated and detected with avidin or streptavidin conjugated to detectable protein, such as streptavidin-horseradish peroxidase. In other examples, the antibody can be conjugated to detectable proteins that permit direct detection, such as, for example, conjugated to a fluorescent protein, bioluminescent protein or enzyme. Various enzymatic staining methods are known in the art for detecting a protein of interest. For example, enzymatic interactions can be visualized using different enzymes such as peroxidase, alkaline phosphatase, or different chromogens such as DAB, AEC or Fast Red. In other examples, the antibody can be conjugated to peptides or proteins that can be detected via a labeled binding partner or antibody. In an indirect IHC assay, a secondary antibody or second binding partner is necessary to detect the binding of the first binding partner, as it is not labeled. Immunohistochemistry typically includes the following steps: i) fixing said tumor sample with formalin, ii) embedding said tumor sample in paraffin, iii) cutting said tumor sample into sections for staining, iv) incubating said sections with the binding partner specific for the marker of interest (i.e. Vnn1) v) rinsing said sections and optionally vi) incubating said section with a secondary antibody and vii) revealing the antigen-antibody complex with avidin-biotin-peroxidase complex. Accordingly, the tissue tumor sample is firstly incubated the binding partners. After washing, the labeled antibodies that are bound to marker of interest are revealed by the appropriate technique, depending of the kind of label is borne by the labeled antibody, e.g. radioactive, fluorescent or enzyme label. Multiple labelling can be performed simultaneously. Alternatively, the method of the present invention may use a secondary antibody coupled to an amplification system (to intensify staining signal) and enzymatic molecules. Such coupled secondary antibodies are commercially available, e.g. from Dako, EnVision system. Counterstaining may be used, e.g. H&E, DAPI, Hoechst. Other staining methods may be accomplished using any suitable method or system as would be apparent to one of skill in the art, including automated, semi-automated or manual systems. In some embodiments, the resulting stained specimens are each imaged using a system for viewing the detectable signal and acquiring an image, such as a digital image of the staining. Methods for image acquisition are well known to one of skill in the art. For example, once the sample has been stained, any optical or non-optical imaging device can be used to detect the stain or biomarker label, such as, for example, upright or inverted optical microscopes, scanning confocal microscopes, cameras, scanning or tunneling electron microscopes, canning probe microscopes and imaging infrared detectors. In some examples, the image can be captured digitally. The obtained images can then be used for quantitatively or semi-quantitatively determining the amount of the marker in the sample.

Typically, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of expression level of Vnn1 in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of Vnn1 in a group of reference, one can use algorithmic analysis for the statistic treatment of the measured expression levels of Vnn1 in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, the predetermined reference value is determined by carrying out a method comprising the steps of a) providing a collection of tumor samples from subject suffering from the same cancer;

b) providing, for each tumor sample provided at step a), information relating to the actual clinical outcome for the corresponding subject (i.e. the duration of the disease-free survival (DFS) and/or the overall survival (OS));

c) providing a serial of arbitrary quantification values;

d) determining the level of Vnn1 for each tumor sample contained in the collection provided at step a);

e) classifying said tumor samples in two groups for one specific arbitrary quantification value provided at step c), respectively: (i) a first group comprising tumor samples that exhibit a quantification value for level that is lower than the said arbitrary quantification value contained in the said serial of quantification values; (ii) a second group comprising tumor samples that exhibit a quantification value for said level that is higher than the said arbitrary quantification value contained in the said serial of quantification values; whereby two groups of tumor samples are obtained for the said specific quantification value, wherein the tumor samples of each group are separately enumerated;

f) calculating the statistical significance between (i) the quantification value obtained at step e) and (ii) the actual clinical outcome of the subjects from which tumor samples contained in the first and second groups defined at step f) derive;

g) reiterating steps f) and g) until every arbitrary quantification value provided at step d) is tested;

h) setting the said predetermined reference value as consisting of the arbitrary quantification value for which the highest statistical significance (most significant) has been calculated at step g).

For example the expression level of Vnn1 has been assessed for 100 tumor samples of 100 subjects. The 100 samples are ranked according to the expression level of Vnn1. Sample 1 has the highest level and sample 100 has the lowest level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer subject, Kaplan Meier curves are prepared for each of the 99 groups of two subsets. Also for each of the 99 groups, the p value between both subsets was calculated. The predetermined reference value is then selected such as the discrimination based on the criterion of the minimum p value is the strongest. In other terms, the expression level of Vnn1 corresponding to the boundary between both subsets for which the p value is minimum is considered as the predetermined reference value. It should be noted that the predetermined reference value is not necessarily the median value of levels of Vnn1. Thus in some embodiments, the predetermined reference value thus allows discrimination between a poor and a good prognosis with respect to DFS and OS for a subject. Practically, high statistical significance values (e.g. low P values) are generally obtained for a range of successive arbitrary quantification values, and not only for a single arbitrary quantification value. Thus, in one alternative embodiment of the invention, instead of using a definite predetermined reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, according to this specific embodiment of a "cut-off" value, the outcome can be determined by comparing the expression level of Vnn1 with the range of values which are identified. In certain embodiments, a cut-off value thus consists of a range of quantification values, e.g. centered on the quantification value for which the highest statistical significance value is found (e.g. generally the minimum p value which is found). For example, on a hypothetical scale of 1 to 10, if the ideal cut-off value (the value with the highest statistical significance) is 5, a suitable (exemplary) range may be from 4-6. For example, a subject may be assessed by comparing values obtained by measuring the expression level of Vnn1, where values greater than 5 reveal a good prognosis and values less than 5 reveal a poor prognosis. In some embodiments, a subject may be assessed by comparing values obtained by measuring the expression level of Vnn1 and comparing the values on a scale, where values above the range of 4-6 indicate a good prognosis and values below the range of 4-6 indicate a poor prognosis, with values falling within the range of 4-6 indicating an intermediate prognosis.

A further object of the present invention relates to a method of treating a sarcoma in a patient in need thereof comprising administering to the patient a therapeutically effective amount of at least one agent selected from the group consisting of i) a polypeptide (P) having an amino acid sequence having at least 80% of identify with SEQ ID NO:1, ii) a nucleic acid molecule encoding for the polypeptide (P), iii) pantothenate, iv) pantethine and iii) cysteamine (CEA).

According to the invention a first amino acid sequence having at least 80% of identity with a second amino acid sequence means that the first sequence has 80, 81, 82, 83, 84, 85, 86, 87, 88, 89, 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

The polypeptides of the present invention are produced by any technique known per se in the art, such as, without limitation, any chemical, biological, genetic or enzymatic technique, either alone or in combination. For instance, knowing the amino acid sequence of the desired sequence, one skilled in the art can readily produce said polypeptides, by standard techniques for production of amino acid sequences. For instance, they can be synthesized using well-known solid phase method, preferably using a commercially available peptide synthesis apparatus (such as that made by Applied Biosystems, Foster City, Calif.) and following the manufacturer's instructions. Alternatively, the polypeptides of the present invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

As used herein, the term "nucleic acid molecule" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiments, the nucleic acid molecule comprises a nucleic acid sequence having at least 50% with SEQ ID NO: 2. According to the invention a first nucleic acid sequence having at least 50% of identity with a second nucleic acid sequence means that the first sequence has 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second nucleic acid sequence.

In some embodiments, the nucleic acid molecule of the present invention is included in a suitable vector, such as a plasmid, cosmid, episome, artificial chromosome, phage or a viral vector. Typically, the vector is a viral vector which is an adeno-associated virus (AAV), a retrovirus, bovine papilloma virus, an adenovirus vector, a lentiviral vector, a vaccinia virus, a polyoma virus, or an infective virus. In some embodiments, the vector is an AAV vector. As used herein, the term "AAV vector" means a vector derived from an adeno-associated virus serotype, including without limitation, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Retroviruses may be chosen as gene delivery vectors due to their ability to integrate their genes into the host genome, transferring a large amount of foreign genetic material, infecting a broad spectrum of species and cell types and for being packaged in special cell-lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV 1, HIV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g., U.S. Pat. Nos. 6,013,516 and 5,994,136, both of which are incorporated herein by reference. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species. Typically, the nucleic acid molecule or the vector of the present invention include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence, is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

As used herein, the term "pantothenate" or "pantothenic acid" has its general meaning in the art and refers to vitamin B5 (a B vitamin). The IUPAC name is 3-[(2R)-(2,4-Dihydroxy-3,3-dimethylbutanoyl)amino]propanoic acid.

As used herein, the term "pantethine" has its general meaning in the art and refers to a dimeric form of pantetheine, which is produced from pantothenic acid (vitamin B5) by the addition of cysteamine. Pantethine is composed of two molecules of pantetheine linked by a bridging disulfide. The IUPAC name is N-[2-[2-[2-[3-(2,4-Dihydroxy-3,3-dimethyl-butanoyl)aminopropanoylamino]ethyldisulfanyl] ethylcarbamoyl]ethyl]-2,4-dihydroxy-3,3-dimethyl-butanamide.

As used herein, the term "cysteamine" has its general meaning in the art and refers to the 2-aminoethanethiol.

In some embodiments, the patient was previously diagnosed as having a poor diagnosis according to the method as above described.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

By a "therapeutically effective amount" is meant a sufficient amount of the agent of the present invention for reaching a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 4,000 mg per adult per day. Typically, the compositions contain 0.01, 0.05, 0.1, 0.5, 1.0, 2.5, 5.0, 10.0, 15.0, 25.0, 50.0, 100, 250, 500 and 1000 mg of the active ingredient for the symptomatic adjustment of the dosage to the subject to be treated. A medicament typically contains from about 0.01 mg to about 1000 mg of the active ingredient. An effective amount of the drug is ordinarily supplied at a dosage level from 0.0002 mg/kg to about 50 mg/kg of body weight per day, especially from about 0.001 mg/kg to 10 mg/kg of body weight per day.

The agent is administered to the subject in a form of a pharmaceutical composition. Typically, the agent of the present invention can be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to the subjects. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the present invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The agent of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1 shows that Vnn1 suppresses sarcoma development in p16−/−p19−/− mice

Figure 2:
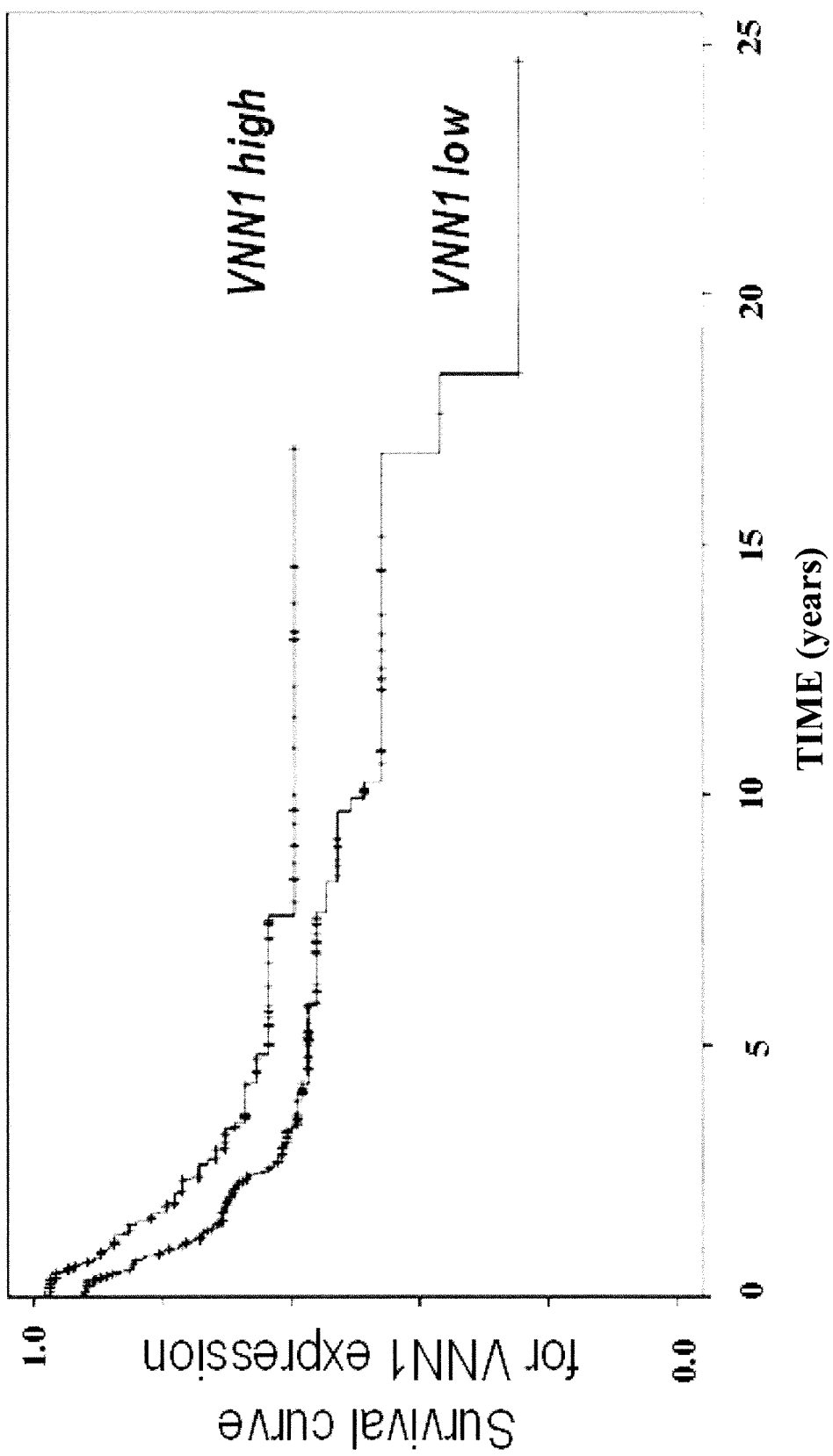
Figure 3:
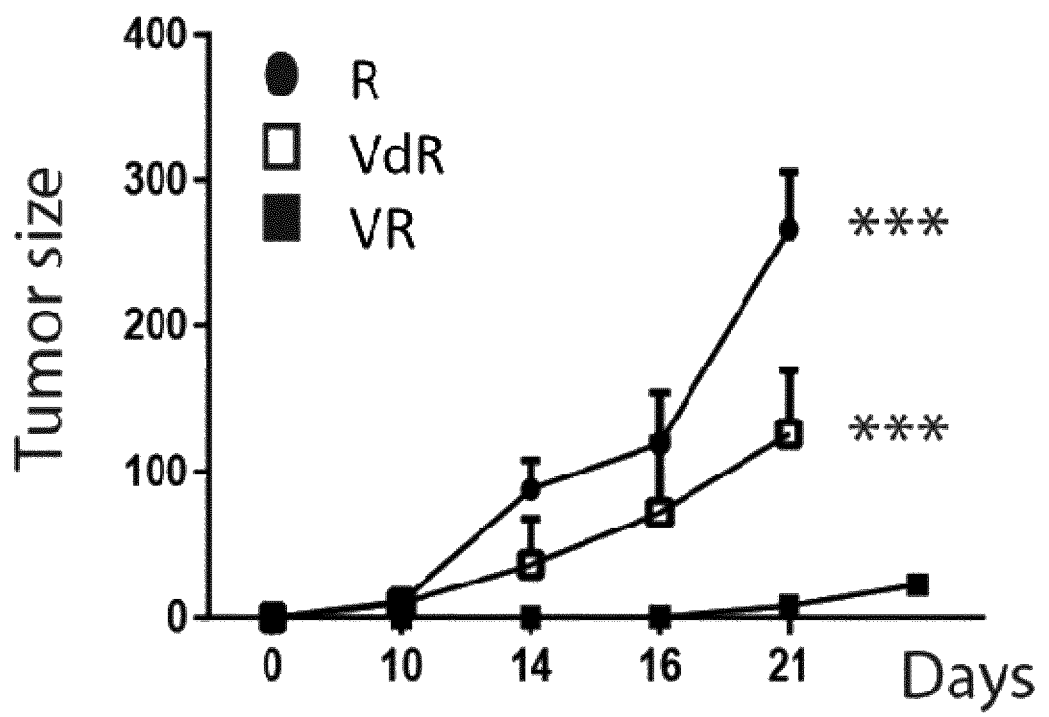
Figure 4:
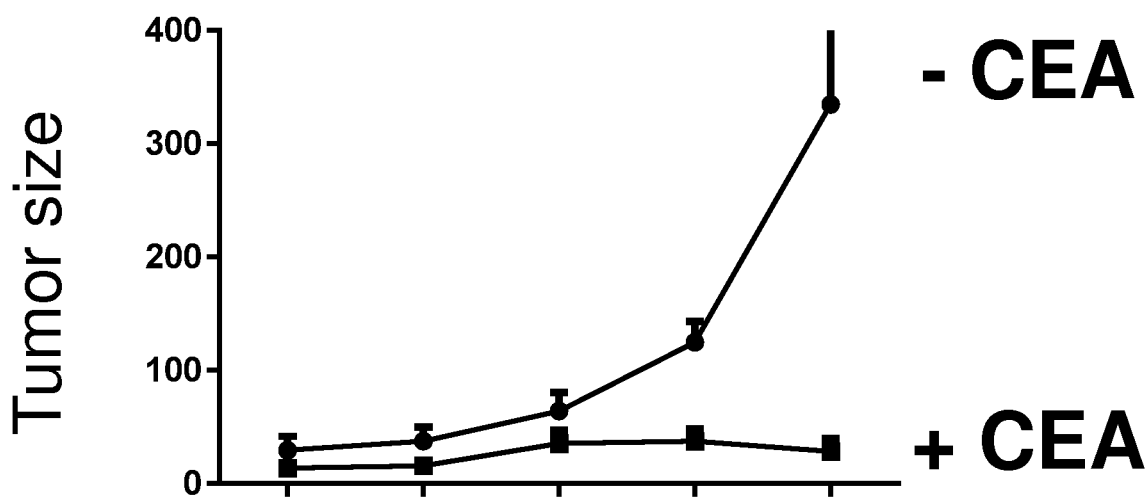

FIG. 2 shows that Vnn1 expression in human sarcomas is associated with reduced aggressiveness and lower risk of metastatic relapse in patients FIG. 3 shows that Vnn1 expression inhibits tumor growth. R: Ras only; VR: Vnn1 and Ras; VdR: catalytically dead Vnn1 and Ras FIG. 4 shows that cysteamine (CEA) inhibits tumor growth FIG. 5 shows the effect of increasing pantetheinase activity in R tumors (A) Scoring of tumor growth in C57BL/6 mice grafted with R or VR cells and receiving pantethine or a mix of cysteamine and pantothenate every other day during the course of tumor development (n=6-8 tumors per condition). (B) Comparative growth of R or R/VR chimeric tumors at two different cell ratios grafted in untreated or pantethine-treated mice. Multiple t tests were performed for statistical analysis.

EXAMPLE

Vnn1 Deficiency Enhances Soft Tissue Sarcoma Development in p16/p19 Deficient Mice Mice bearing a combined deletion of the senescence checkpoints p16 and p19 progressively develop tumors in various tissues. To test the contribution of Vnn1 to spontaneous tumor development, we produced p16/p19/Vnn1 triple KO mice and comparatively scored mouse survival and tumor incidence in three independent cohorts of p16/p19/Vnn1−/− versus p16/p19−/− mice, derived from two independently-derived crosses between p16/p19 KO and Vnn1 KO mice (not shown). As shown in FIG. 1, whereas 35% p16p19−/− mice progressively developed lethal tumors within 25 days as described {Sharpless, 2002 #1775}, 70% p16p19/Vnn1−/− died of aggressive tumors before 200 days (p=0.032). Based on the survival curves, we scored the presence of tumors at the date of sacrifice (200 days or earlier when premature death occurred). 53% p16p19−/− and 65% p16p19/Vnn1−/− mice had developed macroscopic or microscopic tumors at autopsy. Whereas p16p19−/− mice developed various tumor types with a majority of lymphomas (data not shown), p16/p19/Vnn1−/− mice predominantly developed skin STS typed as fibrosarcomas (data not shown). An anatomopathology analysis scored the degree of disorganization and anisonucleosis, the mitotic and necrotic indices and classified tumors from grade I (differentiated) to grade III (undifferentiated). The differentiation grade was further investigated by quantifying the expression levels of collagen 1 and αSMA transcripts (data not shown) which are conventional markers of mesenchymal cell differentiation. In the rare cases of skin STS observed in Vnn1+ mice, the presence of Vnn1 transcripts was confirmed by qRT-PCR (data not shown). These results suggest that Vnn1 can be expressed in STS and may delay their development. In favour of this hypothesis, an analysis of VNN1 transcriptional profile in a large array of human STS suggested that a high level of VNN1 expression is associated with reduced aggressiveness and lower risk of metastatic relapse in patients (FIG. 2).

Vnn1 Exerts a Tumor Suppressive Effect on STS Growth

Given the slow rate of tumor development and the rare emergence of STS in Vnn1+/+ mice, we developed new transplantable STS models. The different tumors derived from three independent myofibroblast cell lines (J2A, H1 or I1) were subcutaneously grafted in Nude mice. As shown in FIG. 3 (extensive results in S2A), Ras expressing tumors (R) grew at high, albeit variable, rates in vivo whereas the expression of Vnn1 by cell lines (VR) considerably reduced their growth rate ($p<10^{-3}$). Tumors expressing the dCr form of Vnn1 (VdR) showed a phenotype similar to Ras-expressing tumors although their growth rate was intermediate (data not shown). Since pantetheinase activity releases pantothenate and cysteamine in vivo, we tested the effect of these compounds on in vitro and in vivo growth. Whereas pantothenate addition had no effect in vitro (data not shown), cysteamine reduced the growth of all cell lines in vitro (data not shown) but also when administered to grafted mice (FIG. 4). These results show that transfection of a catalytically active form of Vnn1 limits tumor cell growth and that cysteamine could participate in this inhibition.

Tumors Derived from Grafted Vnn1-Expressing Cell Lines Display Features of Low Grade STS To evaluate the degree of tumor cell differentiation, an IHC analysis was performed to document the presence of collagen and showed that VR tumors displayed a differentiated phenotype associated with massive collagen production (data not shown), a phenotype reminiscent of primary tumors observed in Ink4A/Arf deficient mice. qRT-PCR analysis showed that VR tumors had higher levels of collagen 1 and caveolin1 transcripts than R and VdR tumors (data not shown). Interestingly, caveolin 1 which is involved in the regulation of receptor activity at the membrane, is downregulated in many tumors with a poor prognostic. We then performed a similar analysis using RNA extracted from enriched R, cysteamine-treated R and VR tumor cells depleted of CD45+ hematopoietic cells. We obtained similar results between R and VR tumors (data not shown) but cysteamine treatment was not able to induce the expression of collagen I or caveolin I genes associated with a mature phenotype. Therefore, Vnn1 expression is associated with a differentiated grade of tumors which is not recapitulated by CEA administration.

The Vnn1 Pantetheinase Enhances Pantothenate Recycling and CoA Production

Since pantetheinase hydrolyses pantetheine into pantothenate and cysteamine, we searched for more specific actions. We first focused on pantothenate which could be detected by LC-MS analysis. Our results show that VR tumors show higher concentrations of pantothenate (data not shown). Since pantothenate is usually not considered to be limiting in vivo, we decided to investigate whether the levels of coenzyme A. Our results clearly showed that VR tumors have much higher CoA levels than R counterparts whereas CEA administration only moderately enhanced CoA levels. This result is the first to document that Vnn1 pantetheinase expression regulates CoA homeostasis in this sarcoma model of tissue stress. Cysteamine has previously shown to partially inhibit γGCS activity thereby limiting the replenishment of GSH stores in stressed tissues. We therefore quantified GSH levels in tissue extracts and while R and VR tumors had comparable total GSH levels, administration of CEA lead to a reduction in GSH levels (data not shown), confirming that CEA could exert a pro-oxidant effect at pharmacological concentrations. However, we could not detect a significant impact of CEA administration on the various metabolites analyzed by LC-MS which therefore does not recapitulate the Vnn1-mediated effect on tumors despite its inhibitory effect on cell growth. These results suggest that energetic pathways might be differentially regulated in VR versus R tumors. Accordingly, we found some significant variations in the levels of various metabolites involved in the regulation of the TCA cycle.

Increasing Pantetheinase Activity in a Ras Tumor Limits its Growth

Figure 5A:
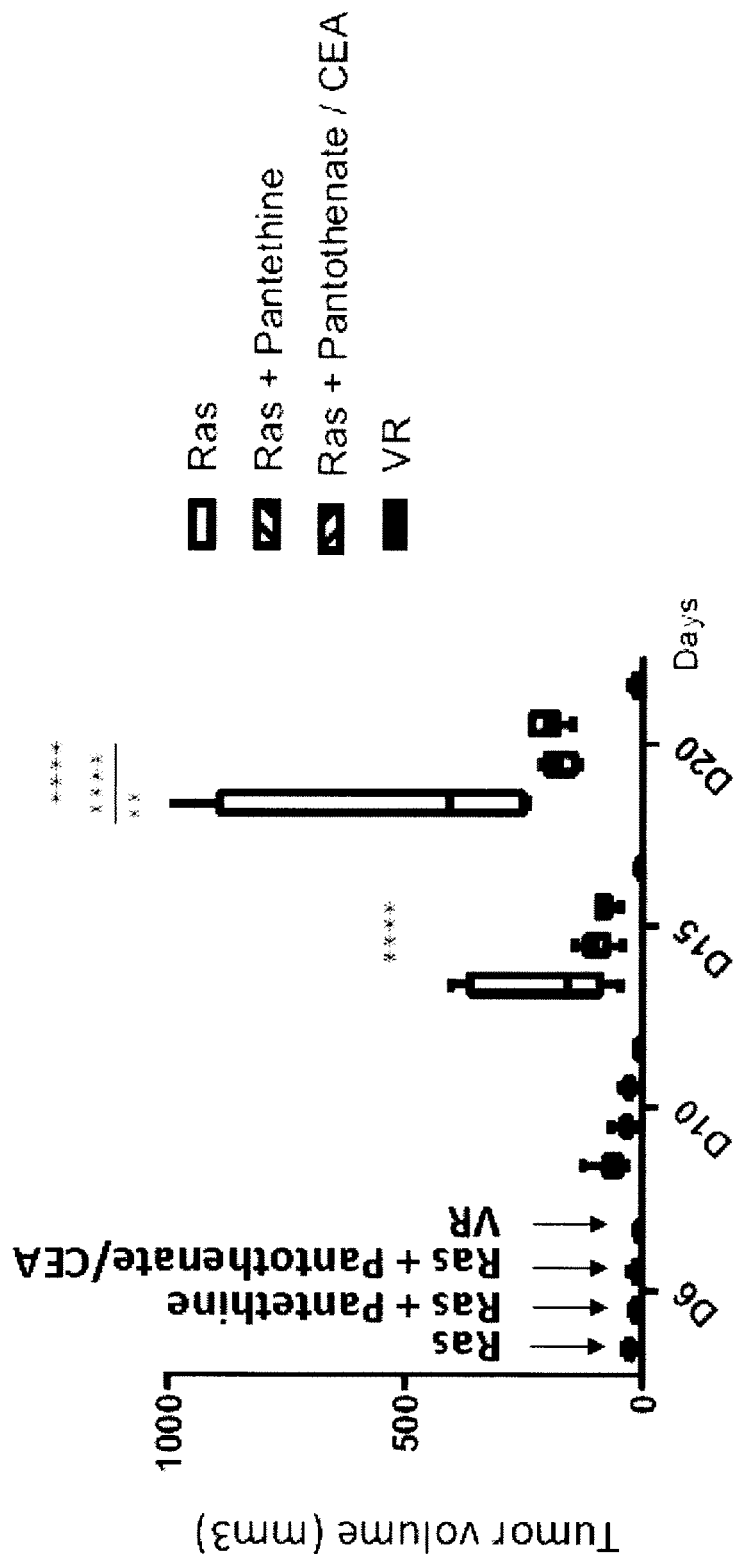
Figure 5B:
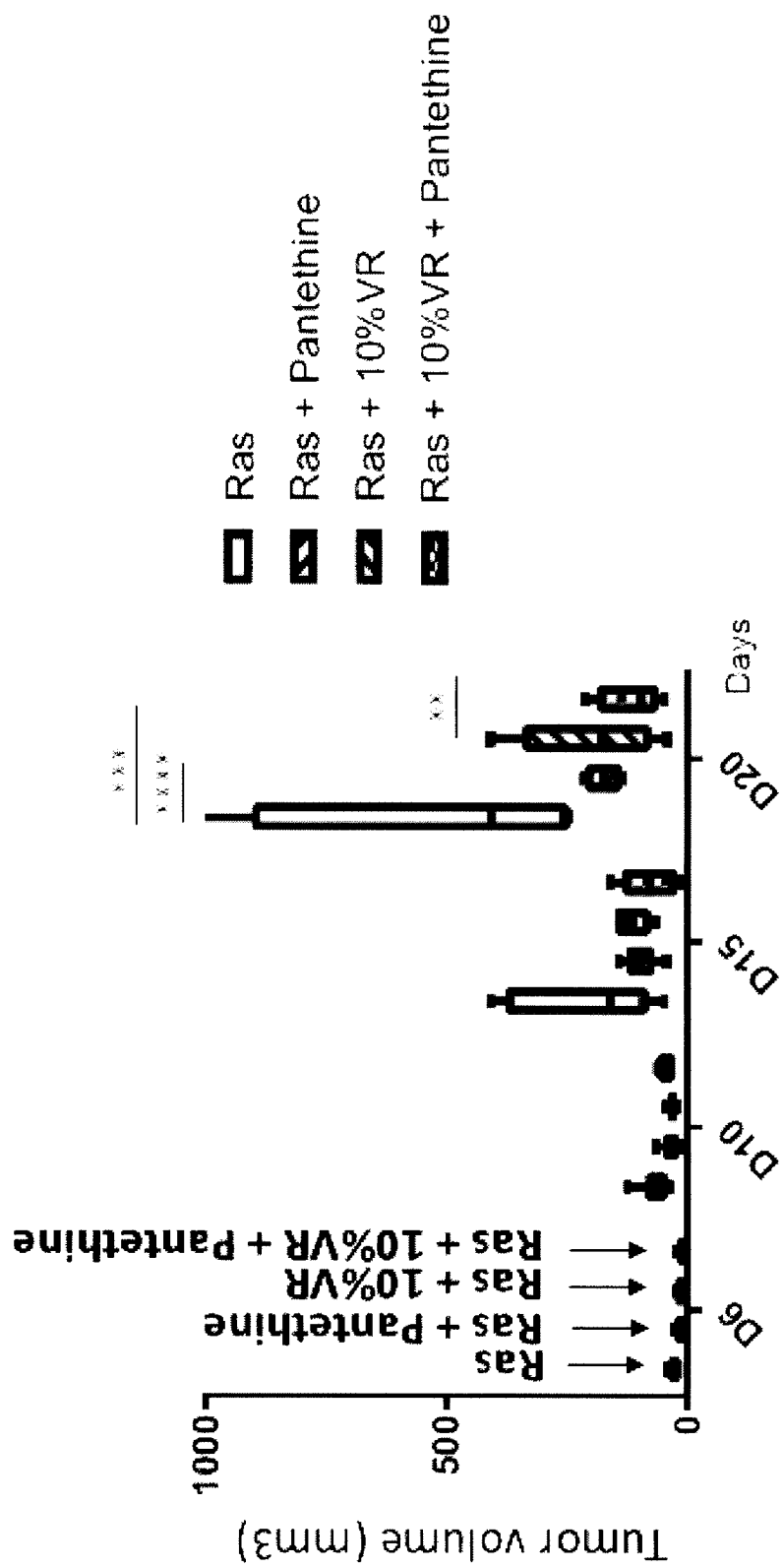

In vivo, tumors are heterogeneous and may contain various proportions of Vnn1$^+$ and Vnn1$^-$ cells. Furthermore, although Vnn1 expression levels are quite variable in tissues, one may wonder whether serum Vnn1 levels might be sufficient to compensate for the loss of Vnn1 expression in tumors. It has been previously shown that pantethine, the oxidized (disulfide) form of PantSH, can be converted in vivo into cysteamine and pantothenate and has significant biological effects in infectious or inflammatory models-We first verified that pharmacological doses of pantethine could reduce the growth of R tumors to a level comparable with that of a combination of cysteamine and pantothenate (FIG. 5A). Next, we set out to determine whether a minimal amount of pantetheinase activity within the tumor mass would potentiate the antitumor effect and be able to control the growth of aggressive R tumors. To test this hypothesis, we injected a mix of R/VR tumor cells at a 10/1 cell ratio in immunocompetent C57BL/6 mice and, additionally, administered pantethine. Interestingly, the presence of 10% VR cells in an R tumor reduces tumor growth, and this inhibitory effect is further enhanced by the addition of pantethine to mice (FIG. 5B). Therefore, this experiment shows that a minimal amount of intra-tumor pantetheinase activity is required to generate a tumor suppressive context in aggressive tumors and suggests that the products of pantetheinase activity work in a paracrine mode on Vnn1$^-$ tumor cells.

REFERENCES

Throughout this application, various references describe the state of the art to which this invention pertains. The disclosures of these references are hereby incorporated by reference into the present disclosure.

The invention claimed is:

1. A method of predicting the survival time of a patient suffering from a sarcoma comprising,
   i) determining the activity or expression level of vanin-1 (Vnn1) in a tumor tissue sample obtained from the patient,
   ii) comparing the level determined at step i) with a predetermined reference value and
   iii) concluding that the patient will have a long survival time when the level determined at step i) is higher than the predetermined reference value or concluding that the patient will have a short survival time when the level determined at step i) is lower than the predetermined reference value.

2. The method of claim 1 wherein the subject suffers from a sarcoma selected from the group consisting of chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

3. The method of claim 1 wherein the patient suffers from soft tissue sarcoma.

4. The method of claim 1 wherein the patient suffers from a fibrosarcoma.

5. A method of treating a sarcoma in a patient in need thereof comprising administering to the patient a therapeutically effective amount of at least one agent selected from the group consisting of i) a polypeptide (P) having an amino acid sequence having at least 80% of identity with SEQ ID NO:1, ii) a nucleic acid molecule encoding for the polypeptide (P), iii) pantothenate, iv) pantethine and iii) a combination of pantothenate and cysteamine (CEA).

6. The method of claim 5 wherein the patient was previously determined as having a poor prognosis by
   i) determining the activity or expression level of vanin-1 (Vnn1) in a tumor tissue sample obtained from the patient,
   ii) comparing the activity or expression level determined at step i) with a predetermined reference value and
   iii) treating the sarcoma in the patient when the activity or expression level determined at step i) is lower than the predetermined reference value.

7. A method of treating a sarcoma in a patient in need thereof comprising administering to the patient a therapeutically effective amount of at least one agent selected from the group consisting of a polypeptide having the amino acid sequence of SEQ ID NO:1, a nucleic acid molecule encoding the polypeptide, pantethine, pantothenate and a combination of pantothenate and cysteamine (CEA).

8. The method of claim 7 wherein the patient was previously determined as having a poor prognosis by
   i) determining the activity or expression level of vanin-1 (Vnn1) in a tumor tissue sample obtained from the patient,
   ii) comparing the activity or expression level determined at step i) with a predetermined reference value and
   iii) treating the sarcoma in the patient when the activity or expression level determined at step i) is lower than the predetermined reference value.

* * * * *